(12) United States Patent
Cosman

(10) Patent No.: US 10,363,369 B2
(45) Date of Patent: Jul. 30, 2019

(54) AMPOULE WITH DUAL LUER FITTING

(71) Applicant: Weiler Engineering, Inc., Elgin, IL (US)

(72) Inventor: Valentin Cosman, Barrington Hills, IL (US)

(73) Assignee: Weiler Engineering, Inc., Elgin, IL (US)

( * ) Notice: Subject to any disclaimer, the term of this patent is extended or adjusted under 35 U.S.C. 154(b) by 580 days.

(21) Appl. No.: 14/596,550

(22) Filed: Jan. 14, 2015

(65) Prior Publication Data

US 2016/0200484 A1 Jul. 14, 2016

(51) Int. Cl.
*A61M 5/24* (2006.01)
*A61M 5/28* (2006.01)
*A61J 1/06* (2006.01)
*A61J 1/14* (2006.01)
*A61M 39/10* (2006.01)

(52) U.S. Cl.
CPC ............ *A61M 5/28* (2013.01); *A61J 1/067* (2013.01); *A61J 1/1481* (2015.05); *A61M 5/24* (2013.01); *A61M 2039/1033* (2013.01)

(58) Field of Classification Search
CPC ............ B65B 43/00; A61M 5/24; A61M 5/28
USPC ............................................. 215/45; 53/452
See application file for complete search history.

(56) References Cited

U.S. PATENT DOCUMENTS

| 5,685,845 | A | 11/1997 | Grimard | |
|---|---|---|---|---|
| 5,901,865 | A * | 5/1999 | Weiler | B65D 23/003 215/46 |
| 6,068,148 | A * | 5/2000 | Weiler | A61J 1/067 141/346 |
| 6,381,926 | B1 * | 5/2002 | Weiler | B65D 23/003 53/420 |
| RE38,399 | E * | 1/2004 | Montgomery | B65D 50/046 215/216 |
| 7,185,790 | B2 * | 3/2007 | Weiler | B65D 1/0238 222/153.06 |
| 8,486,501 | B2 * | 7/2013 | Manabe | A61J 1/067 215/47 |
| 8,636,160 | B2 * | 1/2014 | Park | B65D 50/04 215/201 |
| 2003/0146245 | A1 * | 8/2003 | Weiler | B65D 1/0238 222/420 |
| 2009/0157037 | A1 * | 6/2009 | Iyer | A61J 1/067 604/403 |
| 2014/0299568 | A1 | 10/2014 | Browne | |

* cited by examiner

*Primary Examiner* — Anthony D Stashick
*Assistant Examiner* — Raven Collins
(74) *Attorney, Agent, or Firm* — Olson & Cepuritis, Ltd.

(57) ABSTRACT

A hermetically sealed thermoplastic container or ampoule having a hollow body portion, a neck portion unitary with the body portion and terminating in a circumferential, inwardly extending sealing flange, and a removable cap. The neck portion defines an access passageway to the hollow body portion configured as a Luer female fitting adapted to receive a Luer male connector when the access passageway is open. The outer surface of the neck portion is provided with lugs for engaging a Luer lock male connector and the like.

8 Claims, 4 Drawing Sheets

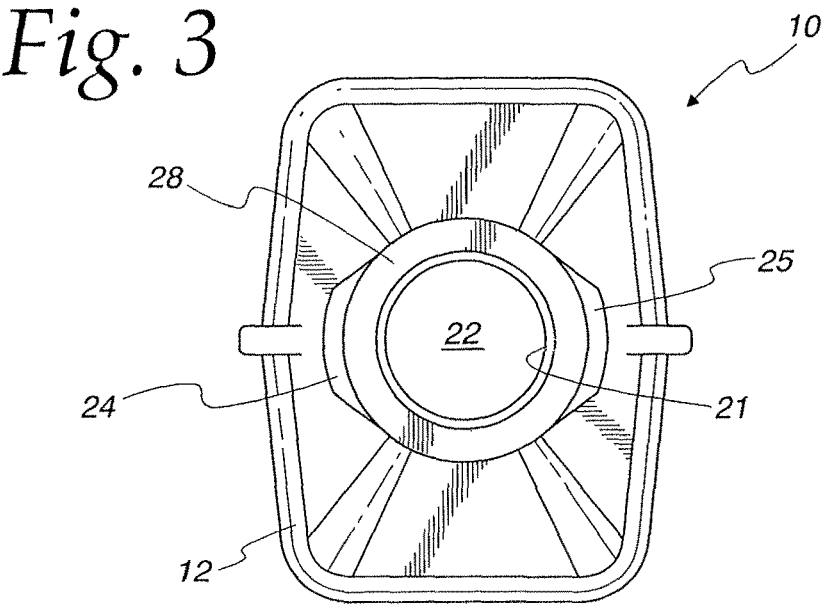
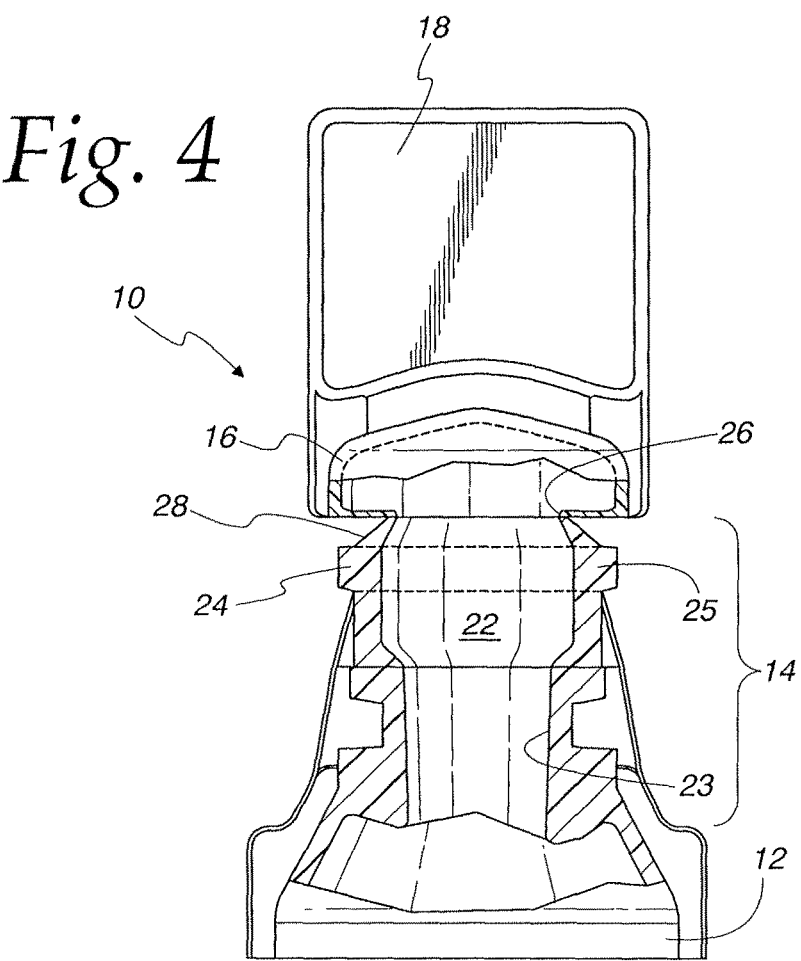

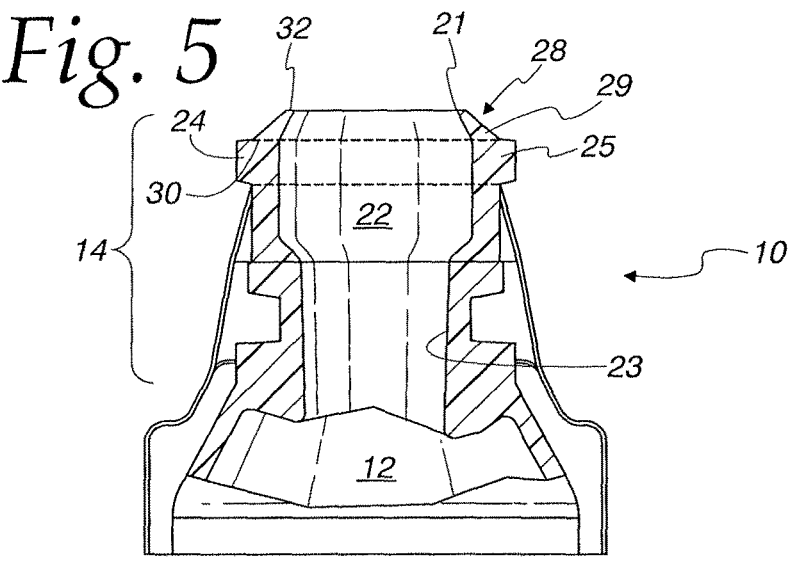
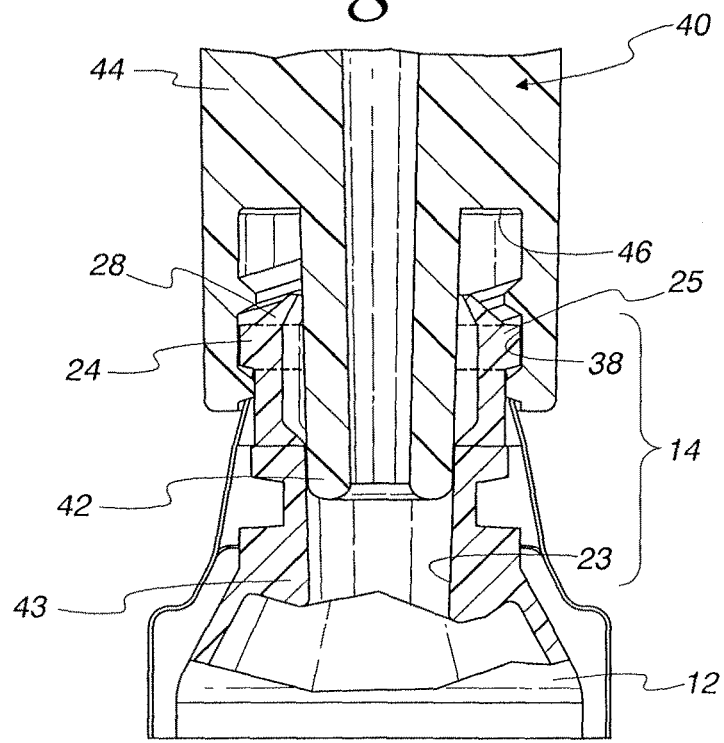

AMPOULE WITH DUAL LUER FITTING

FIELD OF INVENTION

This invention relates to a hermetically sealed thermoplastic container or ampoule with dual Luer fitting.

BACKGROUND OF THE INVENTION

Hermetically sealed containers manufactured by the so-called blow-fill-seal method have enjoyed widespread acceptance for dispensing liquid medicaments and the like.

The Luer taper is a standardized system of small-scale fluid fittings used for making leak-free connections between a male-taper fitting and its mating female part on medical and laboratory instruments, including hypodermic syringe tips and needles. There are two varieties of Luer taper connections: Luer-Lok™ and Luer-Slip™. Luer-Lok™ fittings, generically referred to as Luer lock fittings, are securely joined by means of a tabbed hub on the female fitting which screws into internal threads in a sleeve on the male fitting. Luer-Slip™ fittings, generically referred to as slip tip fittings, conform to Luer taper dimensions and are pressed together and held by friction.

It would be desirable to provide a hermetically sealed thermoplastic container or ampoule with an easily removable cap or closure and with an access passageway sized to receive a variety of implements with Luer taper fittings, such as a Luer-Slip™ or Luer-Lok™ syringe and the like. The present invention provides such a container.

SUMMARY OF THE INVENTION

A hermetically sealed container or ampoule of the present invention is made of a thermoplastic material, such as a polyolefin, and the like, and is provided with a readily removable cap which occludes an access passageway defined by a neck portion of the container. The access passageway may be aligned with the longitudinal axis of the container or ampoule.

A hermetically sealed container embodying the present invention has a hollow body portion that defines a predetermined volume, and a neck portion that is unitary with the body portion and defines an access passageway surrounded by an inwardly extending sealing flange. A removable cap occludes the access passageway. When the cap is removed, the access passageway terminates in an aperture surrounded by an inwardly extending circumferential sealing flange and allows access to the ampoule contents.

Part of the neck portion is configured as a Luer female fitting adapted to receive a Luer male connector when the access passageway is open. Further, the neck portion around its periphery may include external lugs for engaging a Luer lock male connector and the like. The lugs also contribute to rigidity and dimensional stability of the access passageway aperture.

A container or ampoule embodying the present invention comprises a hermetically sealed container of a thermoplastic material having a hollow body portion, a neck portion unitary with the body portion and which terminates in a circumferential, inwardly extending sealing flange. A removable cap is joined to the sealing flange by a frangible web unitary with the removable cap and with the sealing flange. The neck portion of the container defines an access passageway to the hollow body portion and a throat region thereof is configured as a Luer female fitting dimensioned to receive a Luer male connector when the cap is removed and the access passageway is open.

The hermetically sealed container may be provided with a pair of opposed external lugs on the neck portion. The lugs are situated below the sealing flange. The sealing flange may have a quadrilateral cross-section or a trapezoid cross-section.

In a hermetically sealed container with a trapezoid cross-section, the trapezoid has a proximal base adjacent to the neck portion and an opposed distal base that is shorter than the proximal base. Preferably, the proximal base of the trapezoid is at least two times longer than the distal base of the trapezoid, and the distal base of the trapezoid does not overlap the proximal base of the trapezoid.

A removable cap, unitary with the dispensing nozzle occludes the dispensing nozzle and the access passageway. The removable cap is connected at its rim to the dispensing nozzle by a frangible web that is unitary with the cap as well as with the sealing flange that surrounds the access passageway.

The removable cap has an elongated tab or trigger that is unitary with the cap and extends across at least a major part of the top surface of the cap. The tab is positioned across the top surface of the removable cap for engagement therewith when the tab or trigger is manipulated either in a twisting motion or generally about the longitudinal axis of the nozzle. Manipulation of the tab severs the frangible web and permits removal of the cap to gain access to the container or ampoule contents.

BRIEF DESCRIPTION OF THE DRAWINGS

In the drawings,

FIG. 3 is a top view of the ampoule shown in FIG. 1 with the removable cap removed;

FIG. 4 is an enlarged, fragmentary, cross sectional view of the ampoule shown in FIG. 1 with the removable cap in place;

FIG. 5 is an enlarged, fragmentary, cross sectional view of the ampoule shown in FIG. 1 with the access passageway open, i.e., with the removable cap removed;

FIG. 6 shows the ampoule of FIG. 5 with a Luer lock syringe partially engaging opposed lugs on the outer surface of the neck portion;

DETAILED DESCRIPTION OF THE PREFERRED EMBODIMENTS

Figure 1:
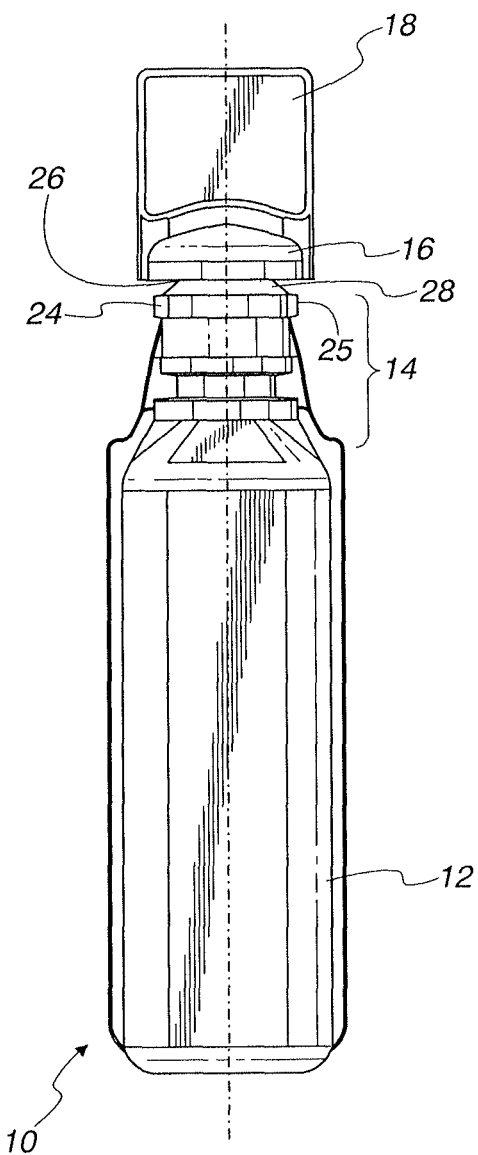
FIG. 1 is a front elevational view of a hermetically sealed ampoule embodying the present invention and with the removable cap in place.
Figure 2:
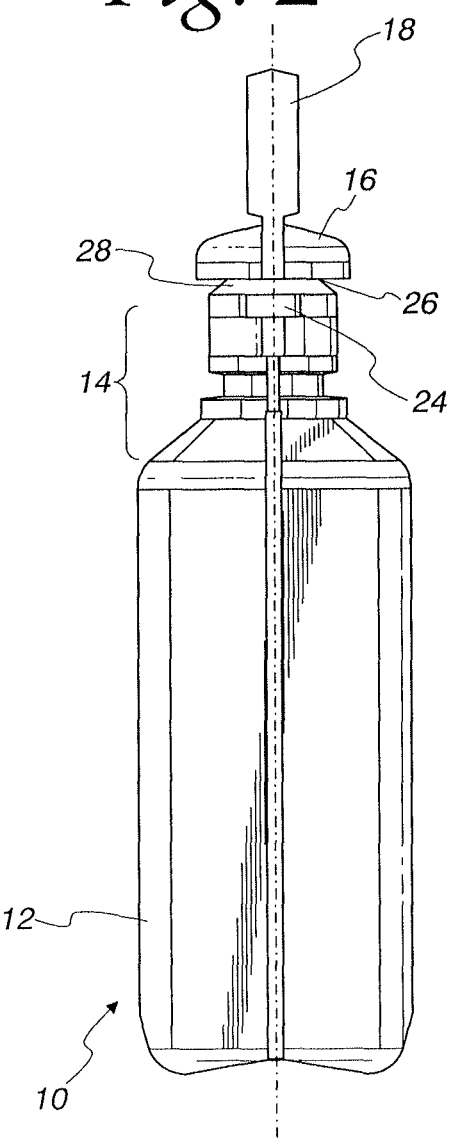
FIG. 2 is a side elevational view of the ampoule shown in FIG. 1.

Referring to the drawings, FIGS. 1 and 2 show hermetically sealed ampoule 10 made of a thermoplastic material such as polypropylene, high density polyethylene (HDPE), and the like. Ampoule 10 has hollow body portion 12 and neck portion 14 unitary with body portion 12. Neck portion 14 defines access passageway 22 having a throat region 23 calibrated as a Luer female fitting (FIGS. 3 and 4), and terminates in circumferential sealing flange 28 which defines aperture 21 (FIG. 3) and is unitary with neck portion 14.

Removable cap 16 occludes aperture 21 and access passageway 22 (FIG. 3), is joined to sealing flange 28 by frangible web 26, and is provided with elongated tab 18 that extends across the top of cap 16. Tab 18 is unitary with cap 16. Manipulation of tab 18 severs frangible web 26 and provides access to passageway 22 as will be discussed in detail below. Opposed lugs 24, 25 sized to engage a Luer lock male connector on a syringe or like device are shown extending outwardly from below sealing flange 28.

FIG. 3 shows a top view of a hermetically sealed ampoule 10 with cap 16 removed. Opposed lugs 24, 25 are axially spaced from throat region 23 to accommodate various Luer syringe designs and configurations. The term "axially spaced," as used herein and in the appended claims, means that throat region 23 is situated inwardly from aperture 21 a predetermined distance sufficient to accommodate Luer lock as well as slip tip male fittings, preferably about 1 to about 1.5 times the largest inside diameter of the Luer female fitting, along the longitudinal axis of passageway 22 defined by neck portion 14.

FIG. 4 shows an expanded cross-sectional view of the upper portion of ampoule 10 with cap 16 attached. Hollow body portion 12 is unitary with neck portion 14, and neck portion 14 in turn is unitary with cap 16. Neck portion 14 also defines access passageway 22 and throat region 23 thereof. Frangible web 26 is unitary with sealing flange 28, so that when tab 18 is manipulated or twisted, force applied to tab 18 will cause frangible web 26 to break and permit removal of cap 16, exposing aperture 21 and access passageway 22 (FIG. 5). Throat region 23 has an inside diameter that is less than the inside diameter of access passageway 22.

An expanded cross-sectional view of the upper portion of ampoule 10 with cap 16 removed is shown in FIG. 5. Body portion 12 is unitary with neck portion 14. Lugs 24, 25 are unitary with neck portion 14 and are sized to engage a Luer lock male connector.

As can be readily seen in FIG. 5, the cross-section 29 of sealing flange 28 is configured as a trapezoid having proximal base 30 adjacent to neck portion 14 and distal base 32. Preferably, and as shown in FIG. 5, distal base 32 does not overlap proximal base 30, and proximal base 30 is approximately twice as long as distal base 32.

Figure 7:
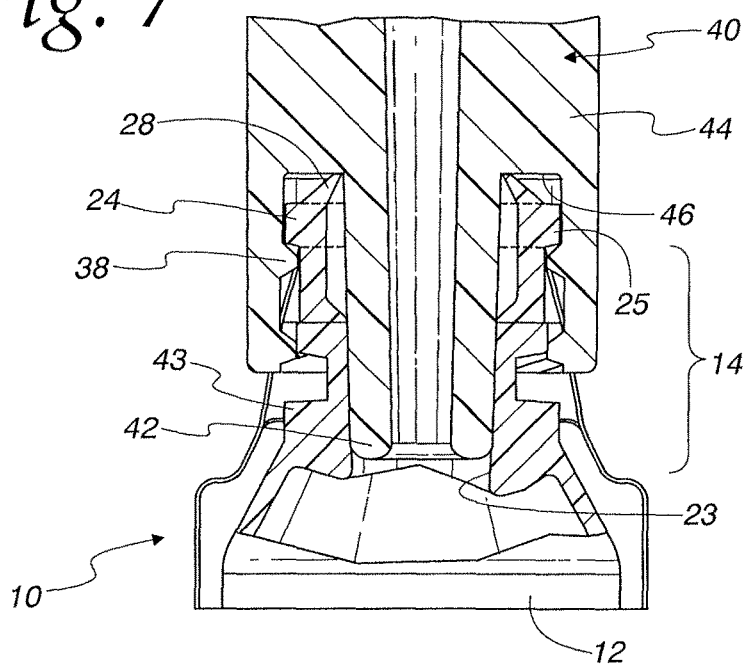
FIG. 7 shows the ampoule of FIG. 6 with the syringe fully threaded on the lugs.

Referring to FIGS. 6 and 7, an expanded cross-sectional view of ampoule 10 is shown. Upper part of body portion 12 merges into and is unitary with neck portion 14. Cap 16 (not shown) has been removed, exposing aperture 21 and access passageway 22. Internal thread 38 of Luer lock syringe 40 is shown engaged by lugs 24, 25 and syringe tip 42 partially engaged with Luer female fitting 43 (FIG. 6). Syringe 40 is shown completely threaded on neck portion 14 in FIG. 7. When syringe 40 is completely threaded, syringe tip 42 is received in Luer female fitting 43 defined by calibrated throat region 23 within access passageway 22. Sealing flange 28 contacts abutment 46 in syringe body 44 and provides a secondary seal around syringe tip 42.

Figure 8:
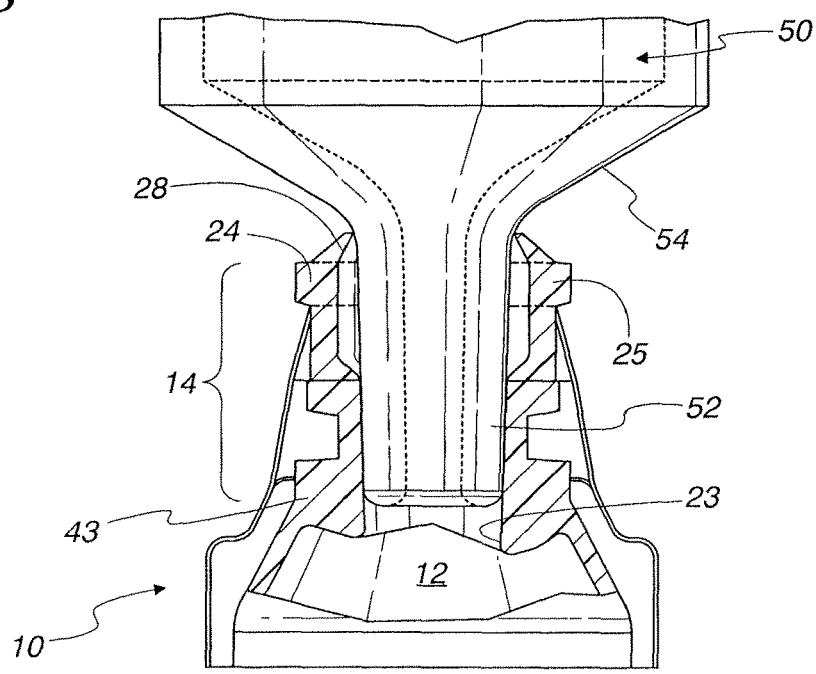
FIG. 8 shows the ampoule of FIGS. 5 and 6 with a slip tip syringe sealingly engaged with the throat region of the access passageway.

FIG. 8 shows an expanded cross-sectional view of ampoule 10 coupled with a slip tip syringe 50. Syringe tip 52 of slip tip syringe 50 is fully received into Luer female fitting 43 at access passageway 22. When syringe 50 is fully inserted, sealing flange 28 engages surface 54 of syringe 50 to form a secondary seal around syringe tip 52.

The ampoule forming, filling, and sealing procedure is well known and is generally described in U.S. Pat. No. 3,597,793 to Weiler et al. Ampoules embodying the present invention can be formed, filled, and sealed under sterile or aseptic conditions using techniques known in the art as described in U.S. Pat. No. 4,178,976 to Weiler et al. Suitable thermoplastic polyolefin materials of construction are polypropylene (PP), high density polyethylene (HDPE), low density polyethylene (LDPE), and the like. A particularly preferred material of construction is polypropylene.

The foregoing description and the drawings are illustrative of the invention, but are not to be taken as limiting. Still other variants within the spirit and scope of this invention are possible and will readily present themselves to those skilled in the art.

The invention claimed is:

1. A hermetically sealed container of a thermoplastic material and comprising a hollow body portion, a neck portion unitary with the body portion and terminating in a circumferential, inwardly extending sealing flange, and a removable cap joined to the sealing flange by a frangible web unitary with the removable cap and with the sealing flange;
the neck portion defining an access passageway to the hollow body portion which includes a throat region configured as a Luer female fitting dimensioned to receive a Luer male connector when the access passageway is open; and a pair of opposed external lugs on the neck portion below the sealing flange.

2. The hermetically sealed container in accordance with claim 1 wherein said throat region is axially spaced from the opposed external lugs.

3. The hermetically sealed container in accordance with claim 1 wherein said sealing flange has a quadrilateral cross-section.

4. The hermetically sealed container in accordance with claim 1 wherein said sealing flange has a trapezoid cross-section.

5. The hermetically sealed container in accordance with claim 4 wherein said trapezoid has a proximal base adjacent to the neck portion and an opposed distal base.

6. The hermetically sealed container in accordance with claim 5 wherein the proximal base of the trapezoid is approximately two times longer than the distal base of the trapezoid.

7. The hermetically sealed container in accordance with claim 5 wherein the distal base of the trapezoid does not overlap the proximal base of the trapezoid.

8. The hermetically sealed container in accordance with claim 1 further provided with a tab unitary with the removable cap.

* * * * *